United States Patent
Itoh

(10) Patent No.: US 8,951,196 B2
(45) Date of Patent: Feb. 10, 2015

(54) ULTRASONOGRAPH

(75) Inventor: Yoshihiko Itoh, Kanagawa (JP)

(73) Assignee: Konica Minolta, Inc., Tokyo (JP)

( * ) Notice: Subject to any disclaimer, the term of this patent is extended or adjusted under 35 U.S.C. 154(b) by 477 days.

(21) Appl. No.: 13/379,694

(22) PCT Filed: Jul. 21, 2010

(86) PCT No.: PCT/JP2010/004682
§ 371 (c)(1),
(2), (4) Date: Dec. 21, 2011

(87) PCT Pub. No.: WO2011/013329
PCT Pub. Date: Feb. 3, 2011

(65) Prior Publication Data
US 2012/0143057 A1    Jun. 7, 2012

(30) Foreign Application Priority Data

Jul. 31, 2009   (JP) ................................ 2009-178691

(51) Int. Cl.
*A61B 8/00*      (2006.01)
*A61B 8/08*      (2006.01)

(52) U.S. Cl.
CPC . *A61B 8/488* (2013.01); *A61B 8/54* (2013.01); *A61B 8/56* (2013.01); *A61B 8/5207* (2013.01)
USPC ............................ 600/437; 600/440; 600/441

(58) Field of Classification Search
USPC ......................... 600/437, 440, 441
See application file for complete search history.

(56) References Cited

U.S. PATENT DOCUMENTS 5,050,611 A    9/1991   Takamizawa et al.
5,882,306 A *   3/1999   Ramamurthy et al. ....... 600/440

(Continued)

FOREIGN PATENT DOCUMENTS

JP    60-024827 A    2/1985
JP    62-227335 A    10/1987
JP    63-240843 A    10/1988

(Continued)

OTHER PUBLICATIONS

Machine Translation of Japanese 07-313508—the Abstract of which was provided within the IDS dated Dec. 21, 2011.*

(Continued)

*Primary Examiner* — James Kish
(74) *Attorney, Agent, or Firm* — Lucas & Mercanti, LLP

(57) ABSTRACT

To provide a small-size ultrasonic diagnostic apparatus manufactured at a low cost, which is capable of displaying an optimum image in both the B mode and the color-Doppler mode, without providing a plurality of drive amplifiers of different transmission voltages to each transmission channel. The ultrasonic diagnostic apparatus has multiple display modes. The ultrasonic diagnostic apparatus includes: a probe for transmitting an ultrasonic beam and receiving a reflection wave of the ultrasonic beam reflected from a tissue of a biological body; a low-pass filter for filtering the reflection wave; and an image processing section for performing on the filtered reflection wave an image process corresponding to a selected display mode. The probe transmits an ultrasonic beam which has an amplitude determined according to the selected display mode. The low-pass filter has such a filter characteristic that at least the cutoff frequency varies according to the selected display mode.

4 Claims, 6 Drawing Sheets

(56) References Cited

U.S. PATENT DOCUMENTS

| | | | |
|---|---|---|---|
| 6,572,546 B1 * | 6/2003 | Bax et al. ................... | 600/437 |
| 2007/0160540 A1 | 7/2007 | Nishigaki et al. | |

FOREIGN PATENT DOCUMENTS

| | | |
|---|---|---|
| JP | 02-098344 A | 4/1990 |
| JP | 07-313508 A | 12/1995 |
| JP | 2004-073883 A | 3/2004 |
| JP | 2008-237280 A | 10/2008 |
| WO | 2006/022106 A | 3/2006 |

OTHER PUBLICATIONS

International Search Report for corresponding International Application No. PCT/JP2010/004682 mailed Aug. 17, 2010.

Form PCT/ISA/237 for corresponding International Application No. PCT/JP2010/004682 dated Aug. 17, 2010 and Partial English translation.

Japanese Office Action dated Jan. 27, 2014 with English translation.

Chinese Office Action, Application No. 201080031610.8, Mailing Date: Mar. 26, 2014 (4 pages).

English translation of Chinese Office Action, Application No. 201080031610.8, Mailing Date: Mar. 26, 2014 (6 pages).

* cited by examiner

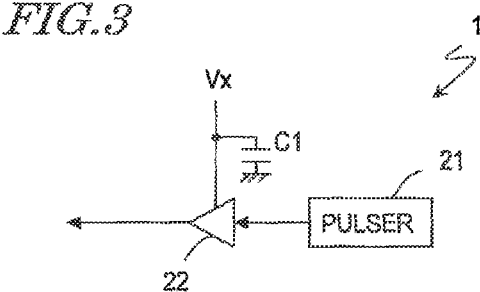
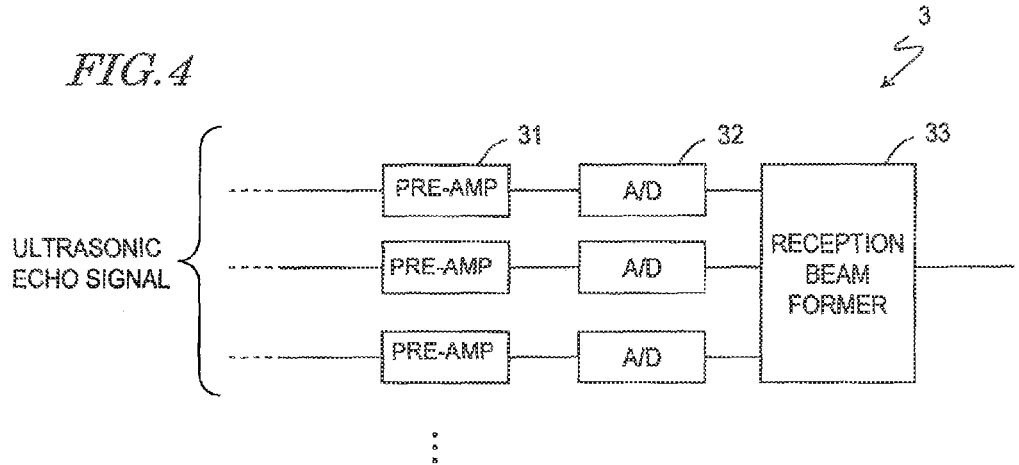

FIG.8
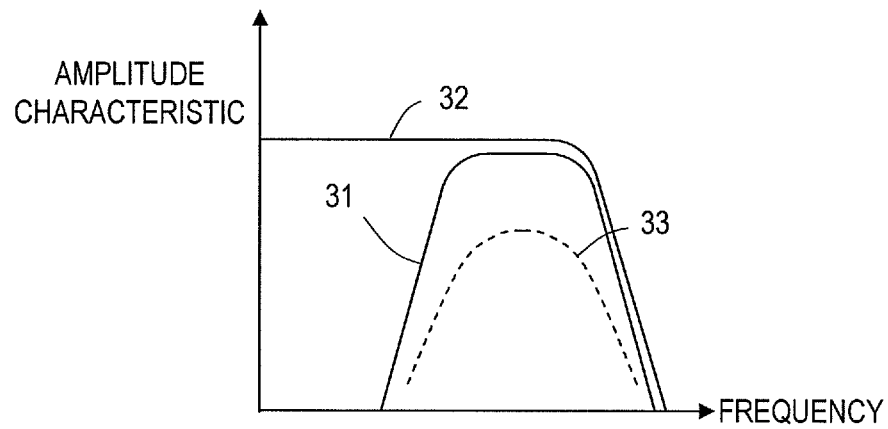
FIG.9
(a) B MODE PULSE IN COLOR-DOPPLER DISPLAY MODE
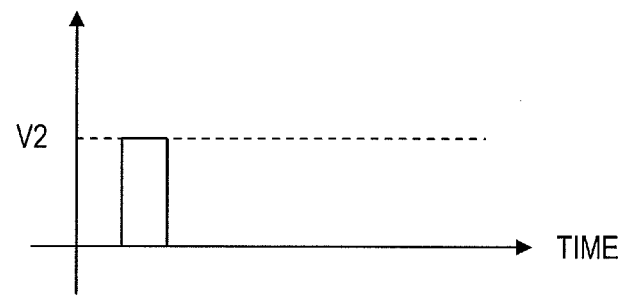
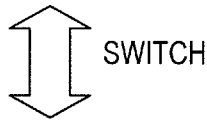 SWITCH
(b) COLOR-DOPPLER PULSE IN COLOR-DOPPLER DISPLAY MODE
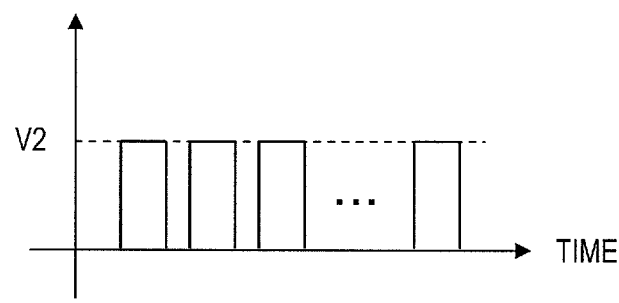

ULTRASONOGRAPH

TECHNICAL FIELD

The present invention relates to an ultrasonic diagnostic apparatus which has multiple display modes (e.g., B-mode function, color-Doppler function, or pulse-Doppler function).

BACKGROUND ART

The ultrasonic diagnostic apparatus enables observation of the internal structure of a body and the blood flow profile in a non-invasive and simple fashion and is therefore used in a wide variety of medical applications.

Many of the ultrasonic diagnostic apparatuses have multiple display modes. For example, the B mode for displaying the information about the physical state of the internal structure of the biological body in the form of a tomographic image, the color-Doppler (CDI, CFM) mode for obtaining the bloodstream information, and the pulse-Doppler (PWD) mode.

The ultrasonic diagnostic apparatus transmits an ultrasonic beam (pulse wave) into the body of a biological body and performs signal processing on a reflection echo signal received via a probe, thereby obtaining biological information. The pulse width, the wave number and the amplitude of the transmitted pulse wave are different among the respective transmission modes such that the optimum reception process is achieved in each of the display modes.

Generally, in the B mode, a wide-band signal, i.e., a short-pulse wave transmission signal that includes about one to two waves, is used. One of the reasons for this is that the B mode is employed in diagnosis of an organ boundary or diagnosis as to whether or not there is a tumor or polyp which is performed based on the physical state information, and therefore, a wide band signal which is excellent in terms of resolution is suitable to this application. On the other hand, in the color-Doppler mode and the pulse-Doppler mode, a narrow-band transmission pulse, i.e., a long-pulse wave transmission signal that includes about four to eight waves, is used. One of the reasons for this is that these Doppler modes are employed in the case where a plurality of pulses are transmitted to and received from one site and the blood flow profile and the bloodstream spectrum are obtained from the relationships among the phases of respective received waves, and therefore, a signal in a specific frequency band (narrow-band signal) is suitable to this case.

To always improve the S/N ratio in the respective modes, the amplitude of a pulse applied to a piezoelectric vibrator may be increased by increasing the transmission supply voltage.

However, to reduce the effect of ultrasonic energy on a biological body, the energy of the transmission signal transmitted from the ultrasonic probe is limited. The energy of the transmission signal depends on the amplitude and the number of vibrations (frequency) of the signal. Therefore, in the color-Doppler or pulse-Doppler mode in which the transmission signal used has a long pulse wave, it is necessary to decrease the transmission supply voltage as compared to the B mode.

One of the existing solutions to this problem is to change the supply voltage for every scan line and controls the pulse amplitude for every transmission mode. To this end, it is necessary to change the supply voltage with an extremely high rate in order to change the supply voltage for every scan line. This may be accomplished by, for example, a technique disclosed in Patent Document 1.

FIG. 12 shows a conventionally-known transmission unit for controlling the pulse amplitude for every one of the transmission modes. This transmission unit includes transmission circuits of two different types which correspond to the respective transmission modes, and two pullers 51, 53 are respectively coupled to two drive amplifiers 52, 54 which are set to different driving voltages. By selectively switching the drive amplifier 52 and the drive amplifier 54 for every transmission mode, the switching is accomplished within a short period of time. Patent Document 1 describes a use with the combination of the B mode and the continuous-wave Doppler mode, although the same applies to the combination of the B mode and the color-Doppler mode and the combination of the B mode and the pulse-Doppler mode.

CITATION LIST

Patent Literature

Patent Document 1: Japanese Laid-Open Patent Publication No. 63-240843

SUMMARY OF INVENTION

Technical Field

The transmission unit shown in FIG. 12 needs to be separately provided to each one of the transmission channels of the ultrasonic probe. In the existing ultrasonic diagnostic apparatuses in recent years, the transmission circuit has 64 to several hundred channels at the maximum. If one transmission unit is provided to each channel, two different types of transmission circuits are necessary. As compared with a single power supply configuration, the required transmission circuit is twofold or more, which leads to a problem that the total circuit scale unduly increases.

Further, appropriately setting two types of transmission supply voltages and carrying out an operation with combinations of different voltages of respective modes complicate measurement of the ultrasonic acoustic power and computation of the Ispta that is deduced from the measured ultrasonic acoustic power and MI, TI references. Thus, setting of the transmission supply voltage for securing the acoustic safety becomes very complicated, resulting in an increased development period.

For the ultrasonic diagnostic apparatuses in recent years, size reduction and weight reduction as well as price reduction have been accelerated along with improved convenience. Even small-size, light-weight apparatuses usually have the color-Doppler display mode. However, the increase of the scale of the transmission unit circuit is a major impediment to that arrangement. Also, the increased development period leads to an increased development cost and delayed timing of release of commercial products into the market, causing loss of opportunities. As a result, it is difficult to provide ultrasonic diagnostic apparatuses with low prices.

The present invention was conceived in view of the above problems. One of the objects of the present invention is to provide a small-size ultrasonic diagnostic apparatus manufactured at a low cost which is capable of displaying images suitable to respective ones of the B mode and the Doppler mode.

Solution to Problem

An ultrasonic diagnostic apparatus of the present invention is an ultrasonic diagnostic apparatus which has multiple display modes, including: a probe for transmitting an ultrasonic beam and receiving a reflection wave of the ultrasonic beam reflected from a tissue of a biological body; a pulser for generating a pulse wave which is determined according to a transmission mode; a transmission circuit which has a drive amplifier whose amplification rate does not vary according to the transmission mode but varies according to a display mode; a low-pass filter for filtering the reflection wave; and a signal processing circuit which includes at least a B-mode signal processing circuit and a color-Doppler or pulse-Doppler signal processing circuit, wherein the low-pass filter has such a filter characteristic that at least a cutoff frequency varies according to a selected display mode.

The filter characteristic of the low-pass filter may be set as follows: if an output amplitude of the ultrasonic beam is greater than a threshold value, the filter characteristic of the low-pass filter is switched to a first low-pass characteristic; if the output amplitude of the ultrasonic beam is equal to or smaller than the threshold value, the filter characteristic of the low-pass filter is switched to a second low-pass characteristic; and a cutoff frequency of the second low-pass characteristic is lower than a cutoff frequency of the first low-pass characteristic.

The filter characteristic of the second low-pass filter may be set such that a higher frequency component of a band of the reflection wave receivable by the probe is partially cut off.

The filter characteristic of the low-pass filter may be set as follows: if the output amplitude of the ultrasonic beam is greater than the threshold value, the filter characteristic of the low-pass filter is switched to the first low-pass characteristic; if the output amplitude of the ultrasonic beam is equal to or smaller than the threshold value, the filter characteristic of the low-pass filter is switched to the second low-pass characteristic; and a gain of a pass band of the second low-pass characteristic is greater than that of the first low-pass characteristic.

Advantageous Effects of Invention

An ultrasonic diagnostic apparatus of the present invention transmits an ultrasonic beam whose amplitude varies according to a display mode selected from multiple display modes. Then, the ultrasonic diagnostic apparatus receives the ultrasonic beam reflected from a tissue of a biological body and subjects the received ultrasonic beam to a low-pass filter. The low-pass filter has such a filter characteristic that at least one of the gain of its pass band and the cutoff frequency varies according to the selected display mode. With such an arrangement, reception band restriction which is imposed according to the transmission output amplitude can be realized. Therefore, a small-size ultrasonic diagnostic apparatus can be provided at a low cost which is capable of displaying a wide band, high frequency B-image with excellent resolution in the single B mode and displaying a B-image with excellent S/N ratio in the color-Doppler display mode.

BRIEF DESCRIPTION OF DRAWINGS

FIG. 3 is a diagram showing a detailed hardware configuration of a one-channel transmission circuit 1.

FIG. 4 is a diagram showing a configuration of a receiving circuit 3.

FIG. 8 is a graph showing a filter characteristic 32 of the low-pass filter 4 in the single B mode.

FIG. 9($a$) is a graph showing the waveform of a B-mode pulse in the color-Doppler display mode. FIG. 9($b$) is a graph showing the waveform of a color-Doppler pulse in the color-Doppler display mode.

DESCRIPTION OF EMBODIMENTS

Hereinafter, an embodiment of an ultrasonic diagnostic apparatus of the present invention is described with reference to the attached drawings.

Figure 1:
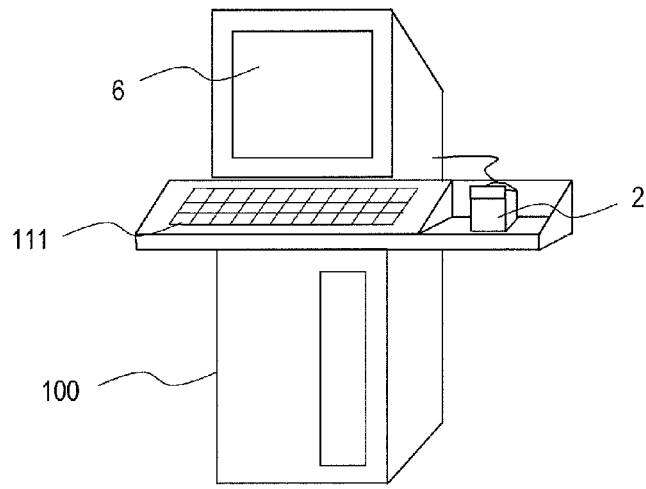
FIG. 1 shows the exterior of an ultrasonic diagnostic apparatus 100 that is an embodiment of the present invention.

FIG. 1 shows the exterior of an ultrasonic diagnostic apparatus 100 of the present embodiment. The ultrasonic diagnostic apparatus 100 displays on a monitor 6 a tomographic image of, for example, an internal tissue of a body with the use of an ultrasonic probe 2. The ultrasonic diagnostic apparatus 100 has multiple display modes, for example, the function of displaying a B-mode image (B-mode function) and the color-Doppler function or the pulse-Doppler function.

These display modes may be selected by an operator through manipulation of various buttons of the ultrasonic diagnostic apparatus 100, for example, buttons 111 of a console panel.

Figure 2:
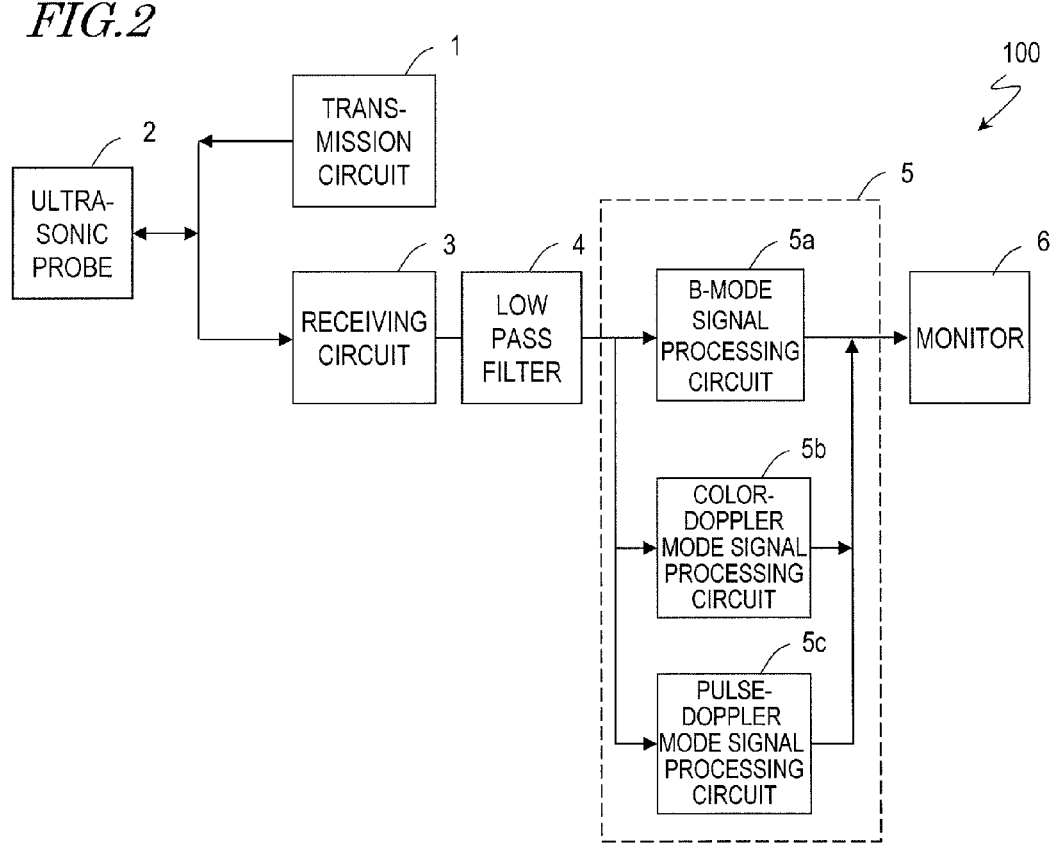
FIG. 2 is a block diagram of the ultrasonic diagnostic apparatus 100 that is an embodiment of the present invention.

FIG. 2 is a block diagram of the ultrasonic diagnostic apparatus 100 of the present embodiment.

The ultrasonic diagnostic apparatus 100 includes a transmission circuit 1, an ultrasonic probe 2, a receiving circuit 3, a low-pass filter 4, a signal processing circuit 5, and a monitor 6. Note that illustration of the buttons 111 of the console panel shown in FIG. 1 is herein omitted.

The transmission circuit 1 drives the ultrasonic probe 2 to transmit an ultrasonic beam. Specifically, the transmission circuit 1 applies to the ultrasonic probe 2 a high voltage pulse wave which has an amplitude equivalent to the transmission voltage. FIG. 3 shows a detailed hardware configuration of the one-channel transmission circuit 1. The transmission circuit 1 may be composed of a plurality of channels (64 channels to several hundred channels), although FIG. 3 only shows part of the configuration corresponding to one channel. It should be noted that the actual transmission circuit includes plural ones of the transmission circuit unit shown in FIG. 3, and the number of transmission circuit units is equal to the number of channels. For example, a 128-ch transmission beam former system includes 128 transmission circuit units of the same configuration which are arranged in parallel.

The transmission circuit 1 includes a pulser 21, a drive amplifier 22, and a capacitor C1. The pulser 21 outputs a low voltage trigger pulse to the drive amplifier 22. Here, the pulsers 21 of the plurality of channels which are in a parallel arrangement output the trigger pulses with appropriate predetermined delay times which are set in the respective pulsers 21. In this way, an ultrasonic beam can be transmitted to a target tissue of a biological body which is at a position specified by target depth and direction. Further, in the present embodiment, the pulser 21 generates pulse waveforms which are different for respective ones of the acoustic scan lines according to the selected display mode. For example, when the B-mode function is selected, the pulser 21 generates a single-wave pulse. When the color-Doppler function is selected, the transmission is performed in such a manner that the B-mode transmission and the color-Doppler transmission are switched at short intervals. Here, the pulser 21 generates a single-wave pulse in the case of the B-mode transmission and generates a four-wave pulse in the case of the color-Doppler transmission.

The drive amplifier 22 amplifies the output of the pulser 21 to a drive voltage Vx. The drive voltage Vx is set to an appropriate voltage according to the display mode. In other words, the drive amplifier 22 changes the degree of amplification depending on, for example, whether to select the B-mode function or the color flow mode function. As a result, the amplitude of the output pulse varies. The capacitor C1 is coupled in parallel to the drive voltage Vx for the purpose of voltage stabilization. The output of the drive amplifier 22 is coupled to a corresponding vibrator of the ultrasonic probe 2.

Figure 12:
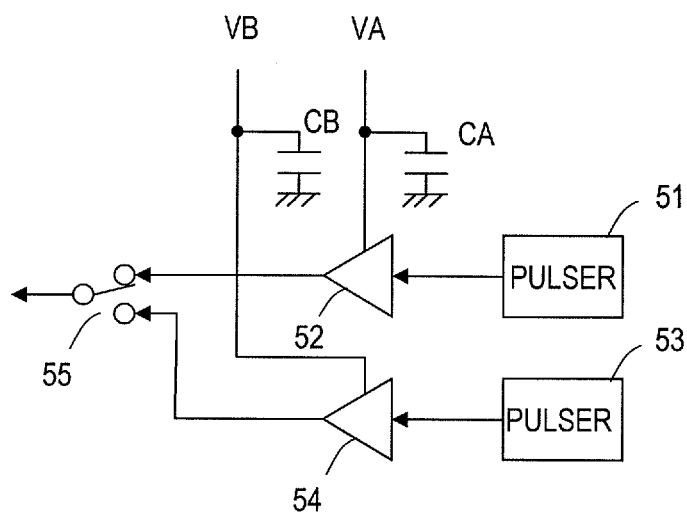
FIG. 12 is a diagram showing a conventionally-known transmission unit for controlling the pulse amplitude for every one of the transmission modes.

It should be noted that the pulser 21, the drive amplifier 22 and the supply voltage for driving, which are shown in FIG. 3, are solely provided to each channel, as compared to the transmission unit shown in FIG. 12 in which multiple pieces of these components are provided to each channel.

The ultrasonic probe 2 electroacoustically converts a high voltage pulse wave supplied from the transmission circuit 1 and transmits the converted wave in the form of an ultrasonic beam into the body. Then, the ultrasonic probe 2 receives a reflection echo signal from a living tissue inside the body and converts the received signal to an electric signal which is then transmitted to the receiving circuit 3.

FIG. 4 shows the configuration of the receiving circuit 3.

The receiving circuit 3 has the function of performing reception focusing with the utilization of the received reflection echo signal (ultrasonic echo signal). Specifically, the receiving circuit 3 includes preamplifiers (e.g., preamplifiers 31) provided for respective ones of the channels, AD converters (e.g., AD converters 32) provided for respective ones of the channels, and a reception beam former 33. The preamplifiers 31 amplify weak ultrasonic echo signals. The AD converters 32 convert the amplified ultrasonic echo signals (analog signals) to digital signals. The reception beam former 33 performs delayed addition of the ultrasonic echo signals (digital signals) of the respective channels, thereby uniting the signals of the multiple channels into one signal which is then output therefrom. This output signal is hereinafter referred to as "received echo signal". Note that the received echo signal is a digital signal.

The output of the receiving circuit 3 is supplied to the low-pass filter 4. The low-pass filter 4 has the characteristic of cutting off a high frequency component of the received echo signal generated by delayed combination. This characteristic can be changed for every one of the display modes by changing the filter multiplication coefficient.

Figure 5:
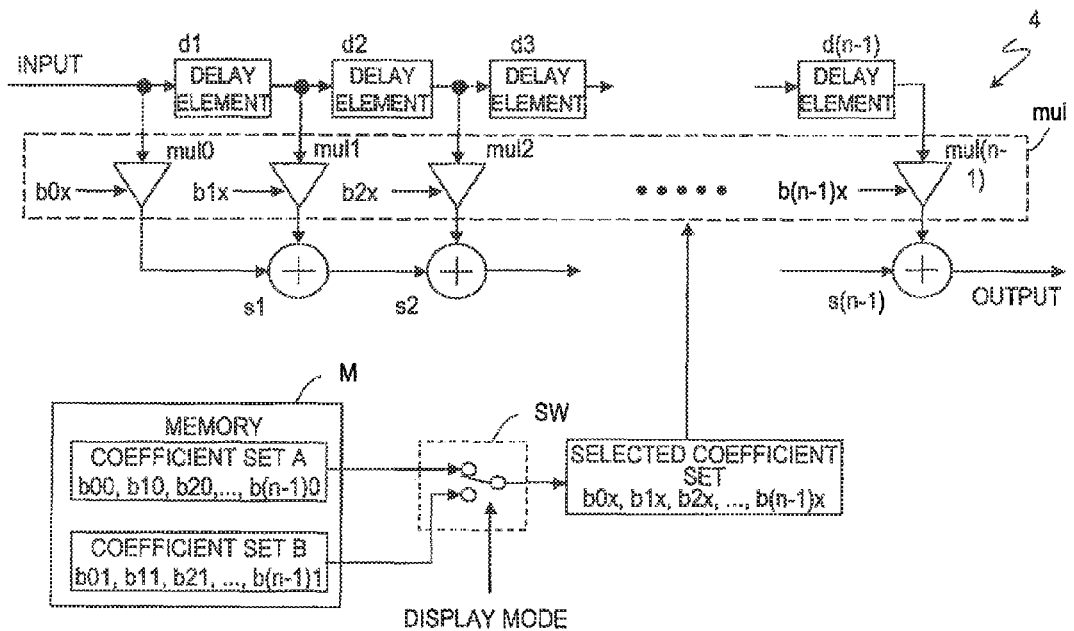
FIG. 5 is a diagram showing a hardware configuration of a low-pass filter 4.

FIG. 5 shows a hardware configuration of the low-pass filter 4. The low-pass filter 4 is, for example, a FIR digital filter.

The low-pass filter 4 includes a plurality of delay elements d1 to d(n-1), a plurality of multipliers mul0 to mul(n-1), and a plurality of adders s1 to s(n-1). Note that FIG. 5 also shows a memory M and a switch SW, although these components are shown for the description which will be provided in the later section. In the present embodiment, the memory M and the switch SW are not included in the components of the low-pass filter 4 but are provided as part of the components of the ultrasonic diagnostic apparatus 100.

Each of the delay elements d1 to d(n-1) holds the received echo signal during one sampling period. The multipliers mul0 to mul(n-1) multiply the respective received echo signals (including received echo signals held in the respective delay elements) by filter coefficients b0x to b(n-1)x that are set in the respective multipliers.

The respective filter coefficients can be switched according to the display mode. More detailed description is now provided. In the memory M of the ultrasonic diagnostic apparatus 100, a plurality of coefficient sets A and B are stored. Each coefficient set is determined according to the selected display mode.

Suppose that, in the ultrasonic diagnostic apparatus 100, the B-mode display and the color-Doppler display are selectable. Here, in the case of the B-mode display, the coefficient set A is selected by the switch SW and applied to the multiplier group mul for utilization in the multiplication in the respective multipliers mul0 to mul(n-1). On the other hand, in the case of the color-Doppler display, the coefficient set B is selected by the switch SW and applied to the multiplication in the respective multipliers mul0 to mul(n-1). The switch SW may be realized by hardware or, alternatively, may be realized by, for example, by the microcomputer (not shown) of the ultrasonic diagnostic apparatus 100 by retrieving any of the coefficient sets.

The respective filter coefficients of the coefficient sets A and B are different, and therefore, the filter characteristic of the low-pass filter 4 varies as the filter coefficients are switched according to the display mode. The detailed description of how it varies will be described later with reference to FIG. 6 to FIG. 11.

Again, refer to FIG. 2.

The output of the low-pass filter 4 is supplied to the signal processing circuit 5. The signal processing circuit 5 includes a B-mode signal processing circuit 5a, a color-Doppler signal processing circuit 5b, and a pulse-Doppler signal processing circuit 5c. The B-mode signal processing circuit 5a performs signal processing, including dynamic filtering, wave detection, log compression, etc. The color-Doppler signal processing circuit 5b performs signal processing, including data rearrangement, MTI filtering, correlation operation, etc. The pulse-Doppler signal processing circuit 5c performs signal processing, including spectrum calculation by means of a FFT operation, etc. The operation results of the respective signal processing circuits 5a to 5c are supplied to the monitor 6. The monitor 6 displays an image based on a received signal. As a result, on the monitor 6, in the case of the B-mode display, a tomographic image of an internal tissue is displayed. In the case of the color-Doppler display or the pulse-Doppler display, an image corresponding to bloodstream information is displayed so as to be superimposed on a B-mode tomographic image.

Each of the B-mode signal processing circuit 5a, the color-Doppler signal processing circuit 5b and the pulse-Doppler signal processing circuit 5c may be provided in the form of a separate hardware circuit. Alternatively, a plurality of image processing programs corresponding to the respective signal processing circuits and one image processing chip may be provided. The image processing chip may selectively execute one of the image processing programs corresponding to the display mode, whereby the signal processing circuits may be realized.

Hereinafter, the operation of the above-described ultrasonic diagnostic apparatus 100 is described.

As previously described in the background art section, many of the ultrasonic diagnostic apparatuses have multiple display modes. The operation state is such that the transmission/reception processes of the respective modes are performed in a complex fashion.

First, the operation of the ultrasonic diagnostic apparatus 100 in an operation mode where only display of a B-mode image that is the most basic display mode is performed (single B mode) is described.

Figure 6:
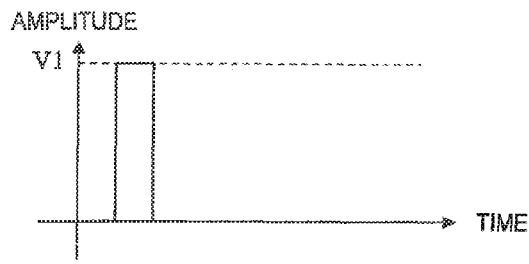
FIG. 6 is a graph showing a transmission pulse from a drive amplifier 22.

The pulser 21 in the transmission circuit 1 transmits a trigger pulse of a short pulse length (e.g., about one to two waves) to the drive amplifier 22. Here, the transmission supply voltage Vx to the drive amplifier 22 is set at the transmission voltage for the B mode (V1). The amplitude of the trigger pulse is amplified to the transmission voltage (V1). FIG. 6 shows a transmission pulse output from the drive amplifier 22. Comparing with the waveform of FIG. 9 which will be described later, this transmission voltage (amplitude) V1 is set to a large level.

Figure 7:
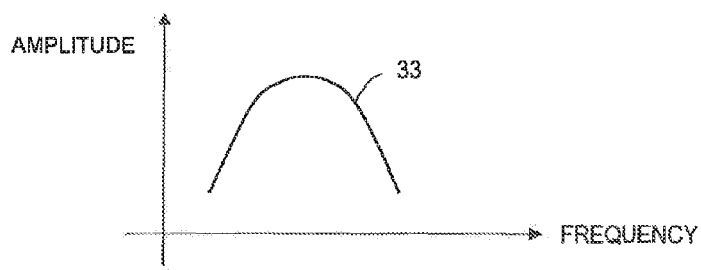
FIG. 7 is a graph showing the frequency distribution 33 of a reflection echo signal.

Next, a reflection echo signal derived from the above transmission pulse is described. For example, FIG. 7 shows the frequency distribution 33 of the reflection echo signal. It is understood that, as compared with the input of a trigger pulse shown in FIG. 6 which is approximate to the impulse, the reflection echo signal derived from the trigger pulse input has a relatively wide frequency band.

The reflection echo from the inside of the body is processed in the receiving circuit 3 and then input to the low-pass filter 4.

FIG. 8 shows the band characteristic and the gain characteristic of the low-pass filter 4 (hereinafter, these are integrally referred to as "filter characteristic") in the single B mode, which is herein represented by the line 32. In FIG. 8, the receivable band 31 of the probe 2 and the frequency distribution 33 of the reflection echo signal of FIG. 7 are shown together. In the single B mode, the band characteristic of the low-pass filter 4 is set so as to have a wide pass band which sufficiently covers the band 31 of the probe 2 as shown in FIG. 8. This filter characteristic 32 is realized by a plurality of filter coefficients b00 to b(n-1)0 which are, for example, defined as the coefficient set A of FIG. 5.

Next, the filter characteristic of the low-pass filter 4 in the color-Doppler display mode is described.

The color-Doppler display mode refers to a complex scan mode where the B-mode transmission cycle and the color-Doppler transmission cycle are alternately switched at short intervals (about several tens of microseconds), whereby both a B-mode signal processed image and a color-Doppler signal processed image are displayed in real time. In the B-mode transmission cycle, the ultrasonic diagnostic apparatus 100 transmits a transmission pulse for the B mode into a body, and a reflection echo signal is processed in the B-mode signal processing circuit 5a and displayed. On the other hand, in the color-Doppler transmission cycle, the ultrasonic diagnostic apparatus 100 transmits a transmission pulse for the color-Doppler into a body, and a reflection echo signal is processed in the color-Doppler signal processing circuit 5b and displayed.

FIG. 9(a) shows the waveform of the B-mode pulse in the color-Doppler display mode. FIG. 9(b) shows the waveform of the color-Doppler pulse in the color-Doppler display mode.

As previously described, the number of pulses of the B-mode transmission pulse is about 1 to 2, while the number of pulses of the color-Doppler transmission pulse is about 4 to 8. Because of the restriction on the ultrasonic acoustic output, the transmission voltage (amplitude) of the color-Doppler transmission pulse cannot be increased to a level which is employed in the single B mode. The transmission voltage in that situation is referred to as "V2". The voltage V2 is smaller than the transmission voltage (amplitude) V1 of the pulse shown in FIG. 6 which is selected in the single B mode (V2<V1).

The pulser 21 in the transmission circuit 1 alternately transmits a B-mode pulse of a short pulse length and a color-Doppler pulse of a long pulse length at short intervals. The transmission voltage supplied to the drive amplifier 22 is set to V2, for both the B-mode pulse and the color-Doppler pulse, for transmission and reception of an ultrasonic wave. In the case of transmitting the B-mode pulse, a transmission wave of amplitude V2, which is relatively small as shown in FIG. 9(a), is transmitted from the drive amplifier 22.

Figure 10:
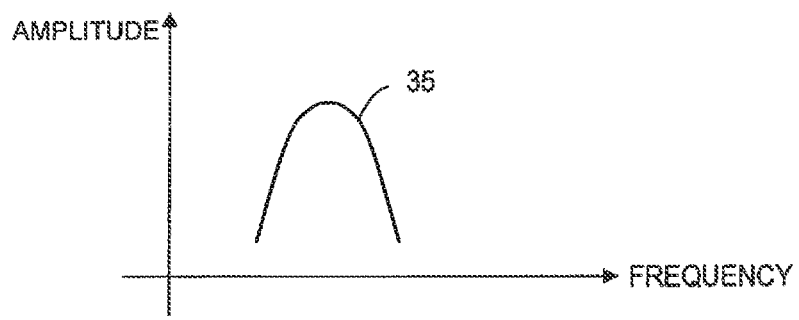
FIG. 10 is a graph showing the frequency distribution 35 of a reflection echo signal of a color-Doppler pulse.

Next, a reflection echo signal derived from the above-described transmission pulse is described. For example, FIG. 10 shows the frequency distribution 35 of the reflection echo signal of the color-Doppler pulse. Comparing with the frequency distribution 33 of FIG. 7, it is understood that the reflection echo signal of the color-Doppler pulse has a relatively narrow frequency band. Note that the frequency distribution of the B-mode pulse in the color-Doppler display mode is as shown in FIG. 7.

The reflection echo from the internal structure of the body is processed in the receiving circuit 3 and then input to the low-pass filter 4. Thereafter, a B-mode image and a color-Doppler image are produced.

As compared to the transmission pulse in the single B mode, the amplitude of the B-mode transmission pulse in the color-Doppler display mode is small. Therefore, the B-mode image in the color-Doppler display mode has a low gain, so that the S/N ratio deteriorates.

Figure 11:
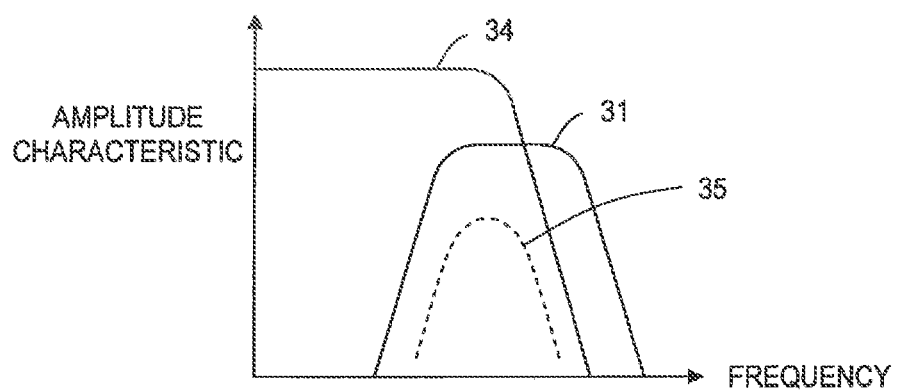
FIG. 11 is a graph showing a filter characteristic 34 of the low-pass filter 4 in the color-Doppler display mode.

To prevent this, the filter characteristic of the low-pass filter 4 is set as shown in FIG. 11. FIG. 11 shows the filter characteristic 34 of the low-pass filter 4 in the color-Doppler display mode. In FIG. 11, the receivable band 31 of the probe 2 and the frequency distribution 35 of the reflection echo signal of FIG. 10 are shown together. In the color-Doppler display mode, the low-pass filter 4 is set such that a higher frequency component of the band of the probe 2 is partially cut off, while the gain of the pass band is increased. Because the ultrasonic attenuation increases as the frequency increases (e.g., the attenuation rate is 0.6 dB/cm·MHz), so that the noise component occurs on the higher frequency side. The pulse voltage is low so that an image is dark, and therefore, it is necessary to increase the gain, thereby increasing the brightness of the image.

The increment of the gain of the pass band (correction amount) may be, approximately, an amount which can compensate for the decrease of the transmission voltage. For example, when the transmission voltage is decreased to 70%, the reception gain may be increased to +3 dB. When the transmission voltage is decreased to 50%, the reception gain may be increased to +6 dB. Note that this specific mode of determining the correction amount is merely exemplary. In actual development, however, the correction amount may be assumed as a parameter for a subject of adjustment, and a developer may determine the correction amount while monitoring a displayed image during an image adjusting operation.

The filter characteristic 34 of FIG. 11 is realized by a plurality of filter coefficients b01 to b(n-1)1 which are, for example, defined as the coefficient set B of FIG. 5.

It is inferred that, when the filter is set to the above-described filter characteristic, the resolution and other factors deteriorate as compared with those of an image produced in the single B mode. However, this is not a significant problem.

In the color-Doppler display mode, the user focuses his attention on the movement of the bloodstream. Therefore, the attention on the B-mode image that is concurrently displayed, particularly the attention on the resolution, is lower than that paid in the single B mode, so that the demand for the image quality resolution decreases. On the other hand, it is appreciated that the B-mode image which is superimposed in the color-Doppler display mode desirably has the image quality of higher S/N ratio, rather than the image quality of wider band and higher frequency.

Next, the correlation between the filter characteristic 32 of FIG. 8 and the filter characteristic 34 of FIG. 11 is described.

First, as for the frequency characteristics, at least the cutoff frequency of the low-pass filter 4 of the present embodiment varies according to the selected display mode. The "cutoff frequency" refers to a frequency at which the gain (amplitude characteristic) of the filter characteristics 32 and 34 starts to decline. Here, the cutoff frequency of the low-pass filter 4 is lower when the color-Doppler mode is selected than when the B mode is selected.

When the color-Doppler mode is selected, the frequency characteristics of the low-pass filter 4 are set so as to partially cut off a higher frequency component of the frequency band of the reflection echo signal which can be received by the probe 2 (receivable band), as illustrated in FIG. 11. On the other hand, when the B mode is selected, the frequency characteristics of the low-pass filter 4 are set such that, for example, the receivable band of the probe 2 is entirely included, as illustrated in FIG. 8. However, in some specifications, part of the receivable band may be cut off.

Next, the gain of the pass band of the low-pass filter 4 is described. The gain of the pass band of the low-pass filter 4 is set so as to be greater when the color-Doppler mode is selected than when the B mode is selected.

In the example of the present embodiment described herein, the low-pass filter 4 is provided between the receiving circuit 3 and the signal processing circuit 5, and the filter characteristic is switched according to the selected display mode. As a configuration example concerning this part, there is a technique of providing a filter in the signal processing circuit 5. For example, the technique of providing a dynamic filter in the B-mode signal processing circuit 5a is known. The dynamic filter refers to a filter which is configured to switch a filter depending on the time and to vary the frequency characteristics for every displayed depth. However, such a dynamic filter is totally different, in terms of function and configuration, from the above-described low-pass filter 4.

The dynamic filter is, firstly, the technique of improving the image quality of the B-mode image, and is a filter which only affects on the image quality of the B-mode image in the single B mode. The characteristics of this dynamic filter are supposed to be deliberately adjusted through lengthy research and examination with many subjects, with consideration for the spatial resolution, the contrast resolution, the S/N ratio, and the image quality balance for each depth.

It is technically possible to achieve an effect which is approximate to the effect of the present invention using the dynamic filter. However, it will take a very long time because adjustment is necessary for meeting the various conditions as described above. The efforts that are necessary for adjustment of the dynamic filter further increase. For example, it is not desirable for development that the efforts are increased two-fold as a result.

In the present embodiment, one static filter, which is not dynamic, is provided before the input of the signal to the dynamic filter for switching of the filter coefficient sets. The filter characteristics of the static filter can be set independent of the dynamic filter, and therefore, the static filter is very simple.

Thus, the filter adjustment is realized by a simple adjustment, i.e., only by determining the cutoff characteristic in the color flow and in the Doppler mode. Therefore, the development period can be greatly shortened.

According to the configuration of the present embodiment, the operation is enabled using other coefficients even in the single B mode. Therefore, additional characteristics which cannot be covered by the dynamic filter characteristics can be provided. This arrangement realizes a steep cutoff characteristic which would not be sufficiently realized by the existing dynamic filter only, and enables control of whether to allow a signal of a specific frequency to pass through and control of the signal amplitude of the allowed signal. It is desirable that the frequency cutoff characteristic of this low-pass filter 4 is appropriately changed depending on the coupled probe, the transmission frequency, or the site of diagnosis.

Thus, according to the ultrasonic diagnostic apparatus of the embodiment of the present invention, a transmission circuit which is common among the respective transmission modes and a low-pass filter whose cutoff band characteristic varies according to the transmission mode contribute to enabling display of a wide band, high frequency B-image with excellent resolution in the single B mode and display of a B-image with excellent S/N ratio in the color-Doppler display mode.

It is not necessary to provide two or more drive amplifiers in the transmission circuit, and the filter itself has a small size. Therefore, the size of the ultrasonic diagnostic apparatus itself can be reduced. Addition of hardware, such as a drive amplifier, greatly affects the increase of the cost and the increase of the power consumption, while addition of a filter can be realized by utilizing existing hardware (e.g., the signal processing section 5) or adding a small and minor circuit element. Therefore, manufacture and utilization at a low cost are possible.

The above-described transmission circuit has been described with an example of binary transmission, although the same applies to an example of bi-polar transmission which uses positive and negative pulses.

In the present embodiment, the color-Doppler mode has been described as an example of the complex mode, although the same operation and effects are also realized in the pulse-Doppler mode, except that the color-Doppler signal processing is replaced by the pulse-Doppler signal processing.

In the example described above, the low-pass filter 4 undergoes a change of the cutoff frequency as well as a correction of the reception gain. However, it is preferred that the low-pass filter 4 only undergoes a change of the cutoff frequency, while the gain correction of the received echo signal is consigned to another signal processing circuit (e.g., the preamplifier).

INDUSTRIAL APPLICABILITY

In an ultrasonic diagnostic apparatus of the present invention, in the case where the display mode is switched among multiple display modes in operation of the apparatus, a filter whose cutoff frequency varies according to the respective display modes is used. The filter characteristics can be adjusted by a simple adjustment, for example, by determining the cutoff characteristics in the color flow and/or the Doppler mode. Therefore, as compared to a conventional method that includes a time-consuming adjustment process which is deliberately performed with body s, the development period can be greatly shortened.

It is not necessary to provide a plurality of drive amplifiers or the like to every transmission channel. Therefore, size reduction and cost reduction can be realized.

REFERENCE SIGNS LIST 1 transmission circuit
2 ultrasonic probe
3 receiving circuit
4 low-pass filter
5 signal processing circuit
5a B-mode signal processing circuit
5b color-Doppler signal processing circuit
5c pulse-Doppler signal processing circuit
6 monitor
21 puller
22 drive amplifier
Vx transmission voltage
C1 capacitor
31 frequency band of probe
32 cutoff characteristic of low-pass filter in single B mode
33 cutoff characteristic of low-pass filter in color-Doppler display mode
51, 53 pulser
52, 54 drive amplifier
VA, VB transmission voltage
CA, CB capacitor
55 switch

The invention claimed is:

1. An ultrasonic diagnostic apparatus which has a single B mode and a complex scan mode, comprising:
a probe configured to transmit an ultrasonic beam having a transmission pulse and receive a reflection wave of the ultrasonic beam reflected from a tissue of a biological body;
a pulser configured to generate the transmission pulse;
a drive amplifier configured to amplify the transmission pulse to produce an output amplitude; and
a low-pass filter configured to filter the reflection wave,
wherein the drive amplifier amplifies each transmission pulse in the complex scan mode so that the output amplitude of the each transmission pulse of the complex scan is the same, and the output amplitude of the each transmission pulse of the complex scan is different from the output amplitude of the transmission pulse in the single B mode, and
a filter characteristic of the low-pass filter varies depending on the output amplitude of the transmission pulse of the ultrasonic beam as follows:
if the output amplitude of the ultrasonic beam is greater than a threshold value, the filter characteristic of the low-pass filter is switched to a first low-pass characteristic;
if the output amplitude of the ultrasonic beam is equal to or smaller than the threshold value, the filter characteristic of the low-pass filter is switched to a second low-pass characteristic; and
a cutoff frequency of the second low-pass characteristic is lower than a cutoff frequency of the first low-pass characteristic.

2. The ultrasonic diagnostic apparatus of claim 1, wherein the filter characteristic of the second low-pass characteristic is set such that a higher frequency component of a band of the reflection wave receivable by the probe is partially cut off.

3. The ultrasonic diagnostic apparatus of claim 2, wherein a gain of a pass band of the second low-pass characteristic is greater than that of the first low-pass characteristic.

4. The ultrasonic diagnostic apparatus of claim 1, wherein a gain of a pass band of the second low-pass characteristic is greater than that of the first low-pass characteristic.

* * * * *